(12) United States Patent
Bernhard et al.

(10) Patent No.: US 8,908,184 B2
(45) Date of Patent: Dec. 9, 2014

(54) ABSORPTION MEASUREMENT SYSTEM

(75) Inventors: Ralf Bernhard, Stuttgart (DE); Achim Gahr, Goldbach (DE)

(73) Assignee: Endress + Hauser Conducta Gesellschaft für Mess- und Regeltechnik mbH + Co. KG, Gerlingen (DE)

( * ) Notice: Subject to any disclaimer, the term of this patent is extended or adjusted under 35 U.S.C. 154(b) by 412 days.

(21) Appl. No.: 13/305,970

(22) Filed: Nov. 29, 2011

(65) Prior Publication Data

US 2012/0140228 A1 Jun. 7, 2012

(30) Foreign Application Priority Data

Dec. 1, 2010 (DE) .......................... 10 2010 062 268

(51) Int. Cl.
*G01N 21/00* (2006.01)
*G01N 21/17* (2006.01)
*G01N 21/85* (2006.01)
*G01N 21/59* (2006.01)

(52) U.S. Cl.
CPC ............ *G01N 21/8507* (2013.01); *G01N 21/59* (2013.01); *G01N 2201/0662* (2013.01)
USPC ......................................... 356/432; 356/433

(58) Field of Classification Search
USPC ................................................. 356/432–444
See application file for complete search history.

(56) References Cited

U.S. PATENT DOCUMENTS

| | | | | |
|---|---|---|---|---|
| 3,680,957 A | * | 8/1972 | Fukuda | .......................... 356/325 |
| 3,843,269 A | | 10/1974 | Hohberg | |
| 3,851,976 A | * | 12/1974 | Meier | ............................ 356/435 |
| 3,995,960 A | * | 12/1976 | Fletcher et al. | ................ 356/433 |
| 4,519,710 A | * | 5/1985 | Luce et al. | ..................... 356/411 |
| 5,268,736 A | * | 12/1993 | Prather | .......................... 356/246 |
| 5,602,647 A | * | 2/1997 | Xu et al. | ........................ 356/435 |
| 5,696,586 A | * | 12/1997 | Ivanov | .......................... 356/364 |
| 6,147,351 A | * | 11/2000 | Huiku | ........................... 250/343 |
| 6,342,948 B1 | * | 1/2002 | Gilby | ............................ 356/436 |
| 6,956,648 B2 | * | 10/2005 | Loicht et al. | ................... 356/323 |
| 7,570,360 B1 | * | 8/2009 | Tkachuk | ........................ 356/437 |
| 7,633,629 B2 | * | 12/2009 | Kiesel et al. | ................... 356/519 |
| 7,781,736 B2 | * | 8/2010 | Logan et al. | ............. 250/339.07 |
| 7,796,261 B2 | * | 9/2010 | Juhl | .............................. 356/435 |
| 7,796,265 B2 | * | 9/2010 | Tkachuk | ........................ 356/437 |

FOREIGN PATENT DOCUMENTS

| | | |
|---|---|---|
| CN | 101042339 A | 9/2007 |
| CN | 101315328 A | 12/2008 |
| DE | 2 258 094 | 5/1974 |

\* cited by examiner

*Primary Examiner* — Tarifur Chowdhury
*Assistant Examiner* — Jarreas C Underwood
(74) *Attorney, Agent, or Firm* — Bacon & Thomas, PLLC (57) ABSTRACT

An absorption measurement system, flexibly usable over a large measuring range, for measuring at least one property of a medium reflected in its absorption behavior, especially a property such as an absorption coefficient (μ). The absorption measurement system comprises: a measuring chamber filled with the medium in measurement operation, in which radiatable beam paths usable as measuring paths and of different lengths, extend completely through the medium; a transmitting unit, which transmits radiation along the measuring paths through measuring chamber in measurement operation; a measuring and receiving unit, which receives radiation passing through measuring chamber on the measuring paths and measures its radiation intensities dependent on the property of the medium and the lengths of the measuring paths; and a measuring electronics, which determines the property based on the measured radiation intensities and the lengths of measuring paths.

18 Claims, 5 Drawing Sheets

ABSORPTION MEASUREMENT SYSTEM

TECHNICAL FIELD

The invention relates to an absorption measurement system for measuring at least one property of a medium reflected in the absorption behavior of the medium, especially a property such as at least one absorption coefficient, comprising a measuring chamber filled with the medium in measurement operation, a transmitting unit, which transmits radiation through the measuring chamber in measurement operation, and a measuring and receiving unit, which receives the radiation passing through the measuring chamber and measures the radiation intensity, which is dependent on the absorption in the medium, and measuring electronics, which determines the property of the medium based on the measured radiation intensity.

BACKGROUND DISCUSSION

Absorption measurement systems are applied today in a large number of industrial applications, especially in the chemical and biochemical industries as well as in water or waste water processing, for measuring absorption characteristics both on line as well as for removed samples. In the case of measuring samples, the measuring chamber regularly has a cuvette fillable with a sample of the medium; the cuvette is inserted into the measuring arrangement and irradiated through a correspondingly placed window of the measuring arrangement. Along with that, there are also absorption measurement systems, which suck the medium into the measuring chamber. In on line measuring, the measuring arrangement is embodied, for example, as a probe, which is brought into the medium. Here the measuring chamber is formed by a cavity in the probe; the cavity is filled by the medium, and the cavity is irradiated through windows mounted on opposite sides of the cavity.

Absorption measurements are executed in different frequency ranges, especially the visible range, the ultraviolet range, or the infrared range under the application of corresponding monochromatic or multifrequency transmission units, depending on application.

The measuring of the radiation intensities emerging from the measuring chamber as a function of the absorption in the medium can occur integrally over a predetermined frequency range or via a spectrometer as a function of frequency.

Absorption coefficients of the medium are regularly measured using absorption measurement systems; for example, the absorption coefficients are determined for a predetermined frequency, as a function of frequency for a predetermined frequency range, or as a variable averaged over a predetermined spectral range.

Other properties, which are reflected in the absorption behavior of the medium, can be determined on the basis of these absorption coefficients using corresponding evaluation methods; such properties include e.g. substances determined to be contained in the medium and/or the concentration of such substances, as well as properties such as e.g. turbidity or coloring. Moreover, other properties, such as e.g. the total organic carbon content or the chemical oxygen demand of the medium can also be derived using corresponding evaluation methods.

Described in U.S. Pat. No. 6,956,648 B23 is an absorption measurement system, embodied as a spectrometric probe, for measuring a property of a medium reflected in the absorption behavior of the medium. The system comprises:

a measuring chamber filled with the medium in measurement operation,
in which radiatable measuring paths of equal length extend completely through the medium;
a transmitting unit, which transmits radiation along the measuring paths through the measuring chamber in measurement operation;
a measuring and receiving unit,
which receives radiation passing through the measuring chamber on the measuring paths and measures its radiation intensities passing through the measuring chamber dependent on the property of the medium; and
a measuring electronics, which determines the property based on the measured radiation intensities and the length of the measuring paths.

A reference chamber bordering the measuring chamber and likewise filled in measurement operation with the medium is additionally provided in the probe described here; reference paths of equal length extend through the reference chamber parallel to the measuring paths in the measuring chamber; the reference paths are shorter than the measuring paths. Changes of the measuring arrangement, such as e.g. age-related changes of the transmission power of the transmission system or the optical transmission systems of the absorption measurement system, are here recognized through a comparison of the optical spectra of the radiation penetrating the measuring chamber on the measuring paths relative to the radiation penetrating the reference chamber on the reference paths.

Absorption measurement systems of the type cited above basically have the problem that the measuring range and the accuracy of measurements achievable in the measuring range depend in high measure on the predetermined length L of the measuring paths. The cause of this is that the radiation intensity $I_0$ emitted by the transmitting unit falls over the predetermined length L of the measuring path in the medium exponentially with the absorption coefficient $\mu$ of the medium. For the radiation intensity I striking the measuring and receiving unit and measured by the measuring and receiving unit, the following equation accordingly applies:

$$I = I_0 e^{-\mu L}$$

Therewith, the measuring range and the achievable accuracy of measurements in the measuring range are fixed by the accuracy, with which the logarithm of the ratio of the transmitted radiation intensity I0 to the measured radiation intensity I divided by the length L of the measuring paths can be determined.

Due to the limited dynamics of today's measuring and recording units, measurements are only possible when the measurement effect, i.e. the difference between the transmitted radiation intensity $I_0$ and the measured radiation intensity I, is sufficiently large, and the absolute values of the transmitted radiation intensity $I_0$ and the measured radiation intensities I lie in a metrologically registerable value range.

As a result, the exact measurement of smaller absorption coefficients $\mu$ requires a large length L of the measuring paths, while the exact measurement of large absorption coefficients $\mu$ requires a comparatively small length L of the measuring paths.

The means that the user can only operate the absorption measurement system in a narrowly limited measuring range due to the predetermined length L of the measuring paths, and the accuracy of measurement achievable sinks toward the edge of the already narrowly limited measuring range.

The field of use of absorption measurement systems with a predetermined measuring path of length L is limited in this way. A flexible use of one and the same absorption measurement system in applications differing as regards the absorption coefficients μ to be measured is not, as a rule, possible.

SUMMARY OF THE INVENTION

It is an object of the invention to provide an absorption measurement system that is flexibly usable over a large measuring range.

For this, the invention resides in an absorption measurement system for measuring at least one property of a medium reflected in its absorption behavior, especially a property such as an absorption coefficient of the medium, comprising
  a measuring chamber filled with the medium in measurement operation;
    in which radiatable beam paths, usable as measuring paths and of different length, extend completely through the medium;
  a transmitting unit, which transmits radiation along the measuring paths through the measuring chamber in measurement operation;
  a measuring and receiving unit,
    which receives radiation passing through the measuring chamber on the measuring paths and measures its radiation intensities dependent on the property of the medium and the lengths of the measuring paths; and
  a measuring electronics, which determines the property based on the measured radiation intensities and the lengths of the measuring paths.

In a first embodiment, the measuring chamber has, in a plane irradiated by the transmitting unit, a wedge shaped cross sectional area, in which the length of the beam paths continuously rises along an axis extending perpendicularly to a main transmission direction of the transmitting unit, in correspondence with an opening angle of the wedge shape.

In a second embodiment, the measuring chamber has, in a plane irradiated by the transmitting unit, a stepped cross sectional area, in which the length of the beam paths rises stepwise along an axis extending perpendicularly to a main transmission direction of the transmitting unit.

In a third embodiment, the measuring chamber has an entrance surface, through which radiation from the transmission system enters into the measuring chamber, and an exit surface, through which radiation escapes from the measuring chamber, and the entrance surface and/or the exit surface are/is a curved area, especially a convex or concave area.

In a further development, the measuring chamber, especially its entrance or exit surface, has a geometry, which has an optical or mechanical function.

In a further development, of the invention
  the measuring paths are a predetermined selection of beam paths, which depends on a measuring range, in which the absorption is to be measured; and
  the measuring and receiving unit measures the radiation intensities of the radiation, which passes exclusively through the measuring chamber on the measuring paths, wherein the radiation intensities are dependent on the absorption in the medium and the lengths of the selected measuring paths.

In a first variant of the further development
  a limited measuring range is predetermined; and
  the measuring paths selected from the beam paths are those beam paths, with which a high accuracy of measurement in this limited measuring range is achieved due to their lengths.

In a second variant of the further development, for achieving a maximal measuring range, all beam paths are selected as measuring paths, and the property is determined based on all radiation intensities received from all measuring paths by the measuring and receiving unit.

In a further development, of the second variant
  there is stored in the absorption measurement system a characteristic curve, which describes a non-linear dependence (characteristic for the measuring chamber and predetermined by the lengths of the measuring paths) of the radiation intensity impinging on the measuring and receiving unit or the ratio of the incoming radiation intensity to the transmitted radiation intensity on the measurable absorption coefficients; and
  the absorption coefficient of the medium located in the measuring chamber in measurement operation is determined based on the incoming radiation intensity measured by the measuring and receiving unit in measurement operation and based on the characteristic curve.

In a first embodiment of the further development
  a system of controllable apertures is inserted into the beam paths outside the measuring chamber; and,
  by controlling the apertures, groups of measuring paths, which extend through the opened aperture or each of the opened apertures, are selectable.

In a second embodiment of the further development, the measuring and receiving unit has individual detectors, especially diodes or CCDs, arranged in a row or an array, and, via these detectors, a separated measurement of the incoming radiation intensities occurs referenced to the positions of the detectors.

In a third embodiment of the further development, the measuring and receiving unit has point shaped or segment shaped radiation receivers terminating externally on the exit surface and arranged distributed over the exit surface, especially in the form of glass fibers or a glass fiber bundle, each of which receivers is connected to a detector, via which a measurement of the incoming radiation intensities referencing the positions of the associated radiation receivers occurs.

Additionally, the invention comprises a method for monitoring a measuring system according to the second or third embodiment, in which
  first, a reference profile is recorded in a reference measurement with a reference medium in the measuring chamber; the reference profile reflects a spatial distribution of the radiation intensities measured with the individual detectors;
  other intensity profiles are recorded in following measurement operations regularly or as needed, the intensity profiles reflect each spatial distribution of the radiation intensities then currently present as measured by the individual detectors; and
  a comparison of the intensity profiles recorded in measurement operation with the reference profile is made to monitor whether zones with an excessively high or low absorption occur in the recorded intensity profiles.

In a fourth embodiment of the further development, the transmitting unit comprises a plurality of emitters, especially emitters with parallel beam guidance, arranged in a row or an array; the emitters can be individually switched on or off as a function of the selection of the measuring paths.

In an additional further development,
  individual predetermined groups of measuring paths are selectable from the beam paths; and
  a frequency selective filter, which is applied in the beam path outside the measuring chamber, is provided for at least one of the groups.

Additionally, the invention comprises a method for operating an absorption measurement system according to the first named further development, in which
- a first measurement is executed with a selection of measuring paths, in the case of which the measuring system has the maximal measuring range;
- based on this measurement, a narrower measuring range, in which the measurement result of the first measuring lies, is established;
- based on this narrower measuring range, a renewed selection of measuring paths, with which the highest accuracy of measurement in this limited measuring range is achievable, is made; and
- following measurements are executed based on this selection of measuring paths for the limited measuring range.

In a further development, of the latter method, the measurement results of the following measurements are monitored, and the selection of the measuring paths is updated as soon as the measurement results come to the edge of, or leave, each limited measuring range last applied.

The invention has the advantage that it is extremely flexibly applicable.

With the measuring system of the invention, on the one hand, by exploiting the total spectrum on different beam path lengths, measurements can now be made in an extremely large measuring range, and, on the other hand, by selecting measuring paths suitable due to their length in individual portions of this large measuring range, a high accuracy of measurement can be achieved.

BRIEF DESCRIPTION OF THE DRAWINGS

The invention and other advantages will now be explained in greater detail based on the figures of the drawing, in which four examples of embodiments are presented. Equal elements are provided with the equal reference characters in the figures. The figures of the drawing show as follows.

DETAILED DISCUSSION IN CONJUNCTION WITH THE DRAWINGS

Figure 1:
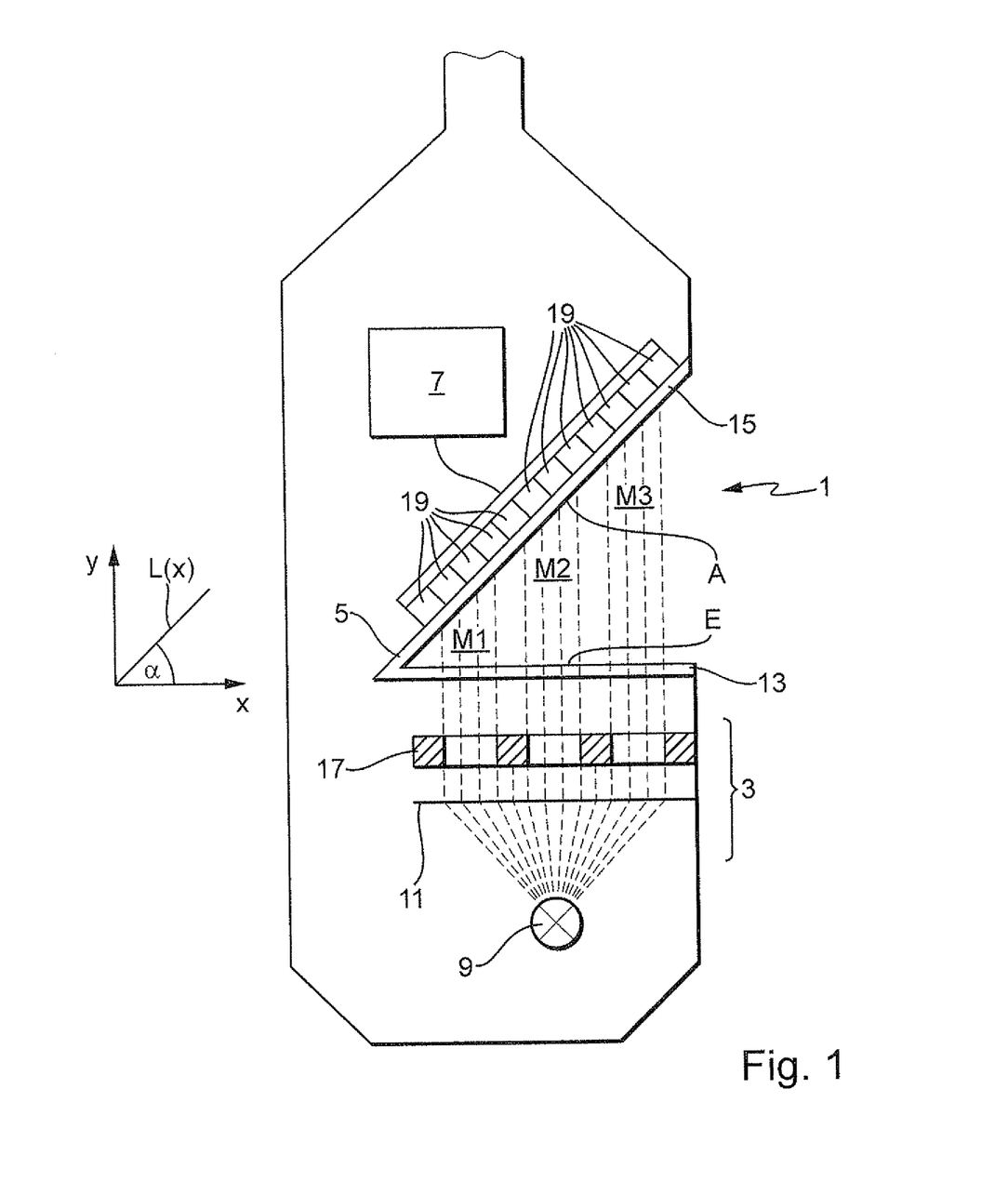
FIG. 1 is an absorption measurement system of the invention having a wedge shaped measuring chamber.

FIG. 1 shows a first example of an embodiment of an absorption measurement system of the invention for measuring at least one property of a medium reflected in the absorption behavior of the medium.

In such case, the absorption coefficients $\mu$ are measured as a main property of the media; the absorption coefficients $\mu$ are determined, depending on the embodiment of the absorption measurement system, for a predetermined frequency, as a function of frequency for a predetermined frequency range, or as a variable averaged over a predetermined spectral range.

On the basis of these absorption coefficients $\mu$, other properties of the medium reflected in the absorption behavior of the medium, such as e.g. certain substances contained in the medium and/or the concentration of such substances, as well as properties such as e.g. turbidity or coloring, can be determined using corresponding evaluation methods. Moreover, other properties, such as e.g. the total organic carbon content or the chemical oxygen demand of the medium can also be derived using corresponding evaluation methods.

The measuring system shown is embodied as a measuring probe, which, for measuring, is immersed in the medium or is flowed around by the medium.

The absorption measurement system comprises a measuring chamber 1 filled with the medium in measurement operation, a transmitting unit 3, a measuring and receiving unit 5, as well as measuring electronics 7. In measurement operation, transmitting unit 3 serves to transmit radiation through measuring chamber 1, which is filled with the medium. For this, transmitting unit 3 comprises, for example, a radiation source 9, e.g. one or a number of photodiodes, whose radiation is sent directly or via a transmission system 11, such as e.g. a light conductor and/or lens system, onto a window 13 facing the transmitting unit 3 and bounding the measuring chamber on this side, through an entrance surface E of measuring chamber 1 and into measuring chamber 1. The radiation penetrating through measuring chamber 1 passes on the opposite side of the measuring chamber 1 through an exit surface O of measuring chamber 1, through a further window 15 bounding the measuring chamber 1 there, to strike measuring and receiving unit 5, which is arranged behind window 15. Measuring and receiving unit 5 receives and measures the incoming radiation intensities I and transmits these to measuring device electronics 7, which are connected thereto; measuring device electronics 7 determines the property of the medium to be measured using corresponding evaluation methods, and provides a display and/or an additional processing.

The invention is also analogously completely applicable in absorption measurement systems, which are not brought into the medium as a probe with open measuring chamber 1, but instead suck the medium into measuring chamber 1 via a corresponding suction system or are equipped with cuvettes containing a sample of the medium. In such case, the cuvette applied in the absorption measurement system forms measuring chamber 1.

According to the invention, radiatable beam paths of different length extend completely through the medium in measuring chamber 1 in measurement operation. This can be realized in very simple and varied manner through the geometry of the cross sectional area of the plane radiated through by transmitting unit 3 in measuring chamber 1. In the example of an embodiment illustrated in FIG. 1, measuring chamber 1 has, for this, a wedge shaped cross sectional area, in which the lengths $L(x)$ of the beam paths continuously increase along an axis X extending perpendicularly to a main transmission direction Y of transmitting unit 3, in correspondence with an opening angle $\alpha$ of the wedge shape.

Figure 2:
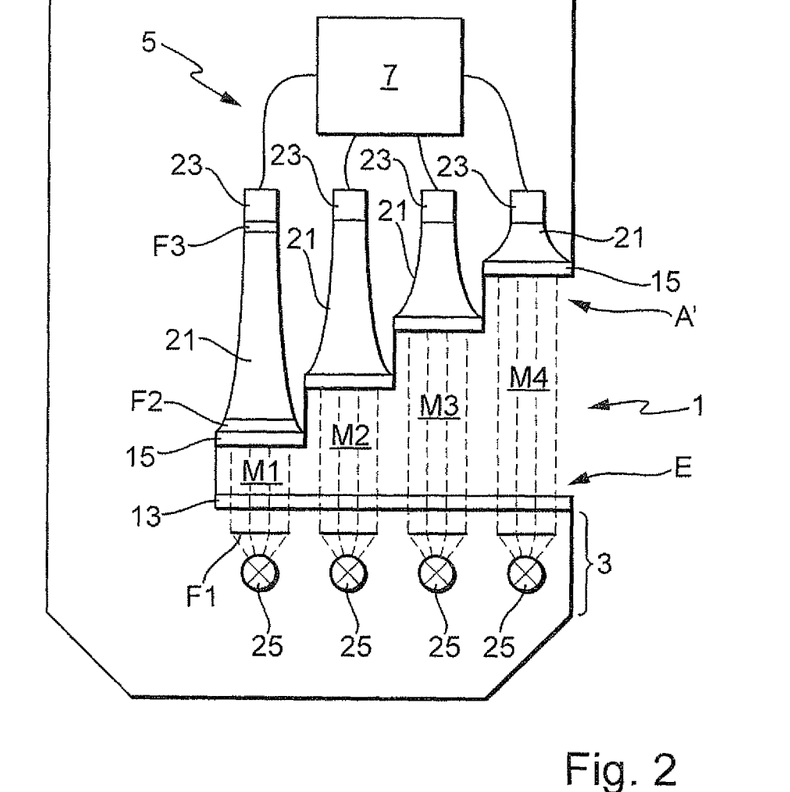
FIG. 2 is an absorption measurement system of the invention having a stepped measuring chamber.

Alternatively, a stepped cross sectional area can also be applied. FIG. 2 shows an example of an embodiment for this, in which the exit surface O', via which the radiation from measuring chamber 1 escapes, is embodied in a stepped manner. Alternatively, the entrance surface E lying opposite exit surface O, via which the radiation enters into measuring chamber 1, can also naturally be embodied in a stepped manner, or both entrance and exit surfaces E, O' can be embodied in a stepped fashion.

Since the geometry of measuring chamber 1, or the geometry of entrance and exit surfaces E, O' is freely selectable within very wide limits for achieving beam paths S of different length, geometries, which fulfill an additional optical or mechanical function, can also be used here.

Figure 3:
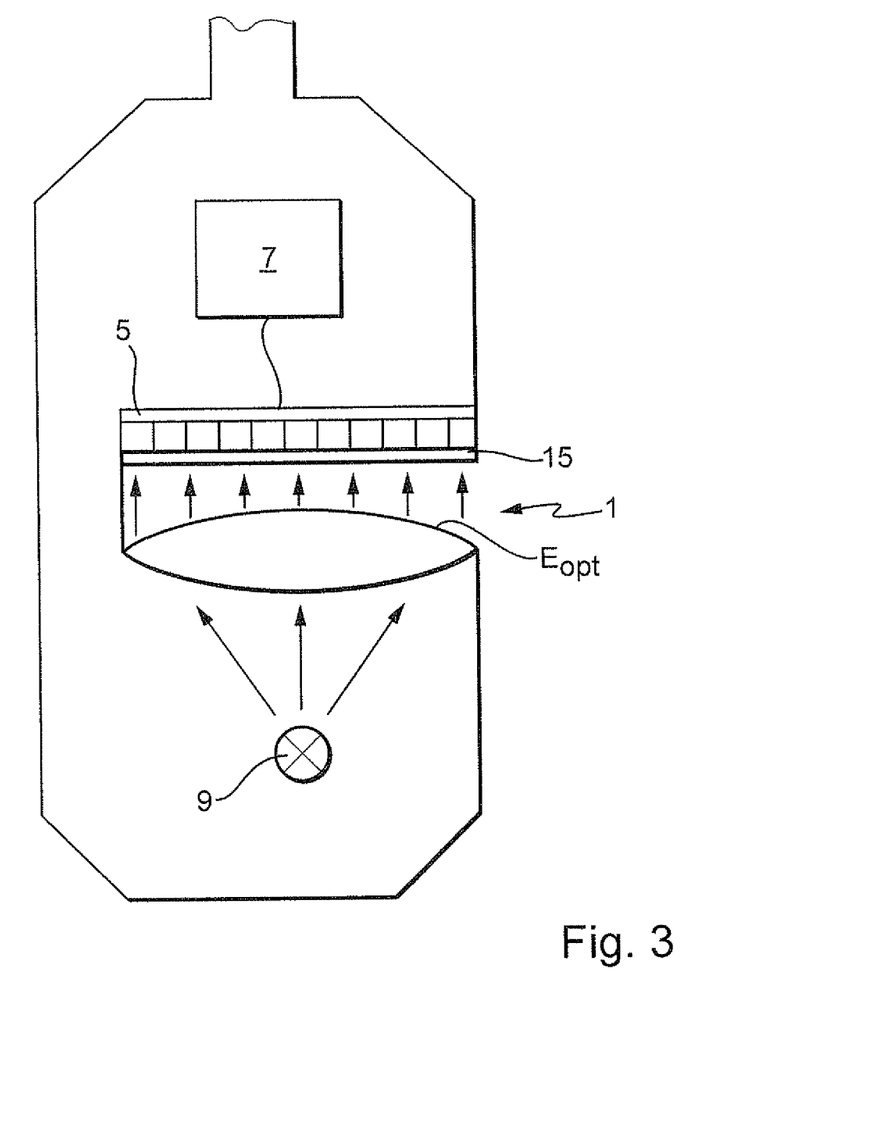
FIG. 3 is an absorption measurement system of the invention having a measuring chamber with a curved entrance surface.

For this, for example, curved, preferably convex or concave, entrance or exit surfaces E, O, which fulfill an optical function at the same time, can be used. Thus, for example, the entrance surface $E_{opt}$ curving into the measuring chamber 1 shown in FIG. 3 serves comparably to a lens for parallel beam guidance.

Figure 4:
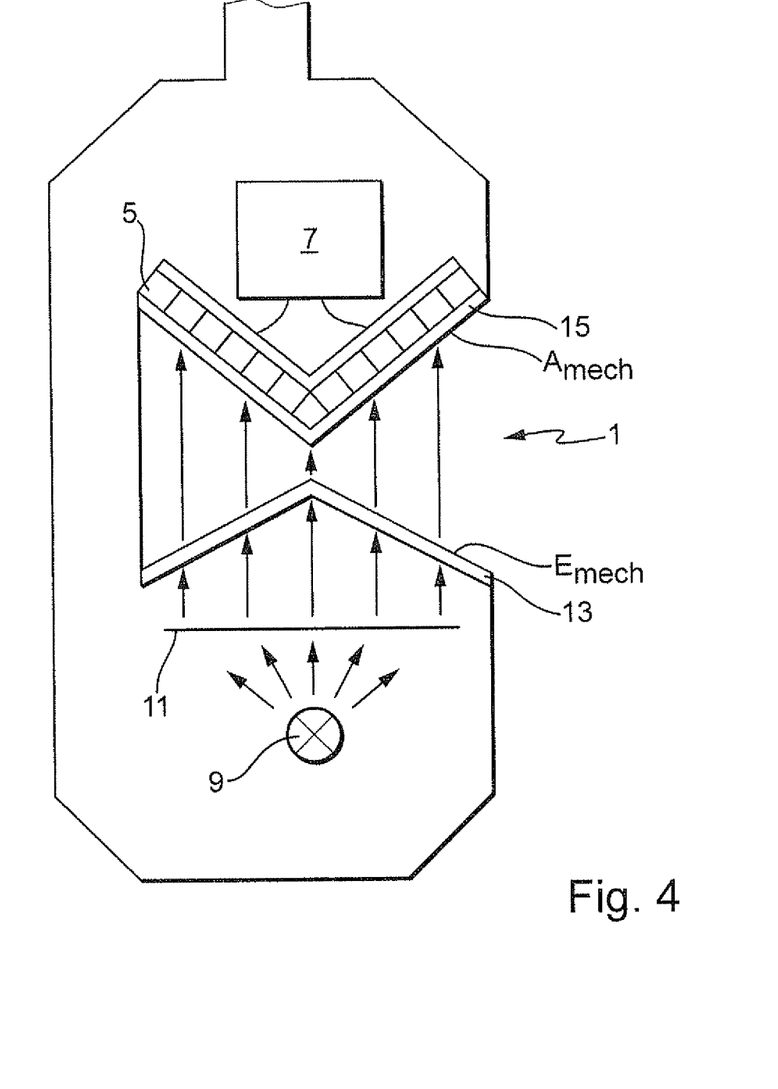
FIG. 4 is an absorption measurement system of the invention having a measuring chamber having cone shaped entrance and exit surfaces.

FIG. 4 shows an example of a measurement chamber geometry with a mechanical supplemental function. Here, the entrance surface $E_{mech}$ and the exit surface $O_{mech}$ each have a geometry tapering toward the center of measuring chamber 1. Entrance surface $E_{mech}$ and exit surface $O_{mech}$, can be embodied, for example, as a peaked roof shape or a cone shape for this. These forms support and accelerate a draining away of drops or bubbles possibly clinging to these surfaces.

Of the beam paths available due to the measurement chamber geometry, basically, for measuring the absorption, a predetermined selection of beam paths, dependent on a measuring range, in which the absorption is to be measured, is utilized as measuring paths M for measuring in measurement operation.

The selection can be made with the goal, for example, of covering a measuring range as large as possible. For this, the selection comprises measuring paths M of clearly different lengths L. Preferably, for this, all beam paths available are selected and used as measuring paths M.

Figure 5:
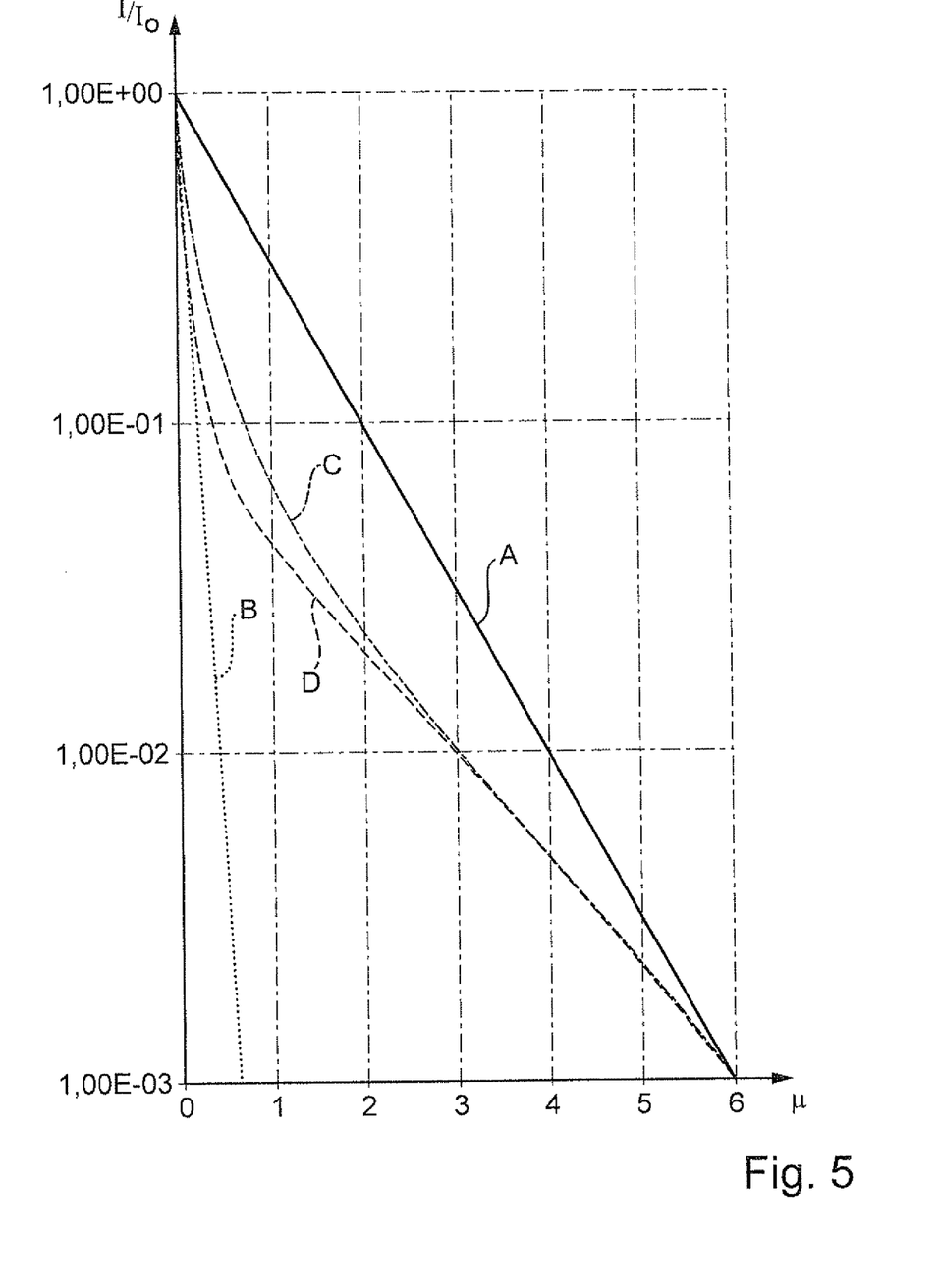
FIG. 5 are logarithmically plotted curves of a relationship of measured radiation intensity to radiated radiation intensity as a function of the absorption coefficients for a number of measurement chamber geometries.

FIG. 5 shows, in this connection, the logarithmically plotted ratio of the amount of measured radiation intensity I to transmitted radiation intensity $I_0$ as a function of the absorption coefficient μ of the medium. Black curve A is for a measuring chamber 1 with a small identical length for all measuring paths; dashed curve B for a measuring chamber 1 with a large identical length for all measuring paths; dark gray curve C for a measuring chamber, in which measuring paths of different length extend with wedge shaped cross sectional geometry; and light gray curve D for a measuring chamber 1, in which part of the measuring paths have an identically short length and the remaining measuring paths have an identically great length, with stepped geometry of only a single step.

The curves A and B have a linear curve due to the equal small or large lengths of all measuring paths in each case; the slope of curves A and B corresponds to the respective measuring path length. Fundamentally, the measurement error, which occurs in the metrological registration of intensity ratios $I/I_0$ of measured radiation intensity I to transmitted radiation intensity $I_0$, is larger, the smaller the absorption related difference between the transmitted radiation intensity $I_0$ and the radiation intensity I measured by measuring and receiving unit 5. The measurement error decreases, thus, first from top to bottom in the representation shown until it then rises again due to the always decreasing absolute value of the radiation intensity I to be measured. The cause for this new rise is especially the always decreasing resolution achievable by measuring and receiving unit 5 in the case of very small radiation intensities I to be measured with declining radiation intensity I. In this way the measuring range of measuring chambers with only one measuring path length is limited to large absorption coefficients μ in the case of a short measuring path length (curve A), and to small absorption coefficients μ in the case of a long measuring path length (curve B).

In comparison with this, curves C and D show a clearly non-linear curve predetermined by the particular measurement chamber geometry due to the simultaneous use of different measurement path lengths. In such case, the measuring paths with larger lengths already affect a clearly measurable decrease of the measured radiation intensity I striking the measuring and receiving unit 5, as a whole, in the case of low absorption coefficients μ. This is shown in the steep falling of curves C and D in the region of smaller absorption coefficients μ. With increasing absorption coefficients μ, the influence of the measuring paths with larger length decreases due to the always decreasing radiation intensity penetrating through the measuring paths. I.e. the fraction of the radiation reaching measuring and receiving unit 5 via the longer measuring paths of the total radiation intensity I striking measuring and receiving unit 5 always decreases with increasing absorption coefficients μ. In parallel thereto, the influence of the measuring paths with lesser length increases due to the decreasing radiation intensity I emerging in measurable amount with increasing absorption coefficient μ.

For each measuring chamber 1, a predetermined, characteristic, unique, non-linear dependence (which is due to the lengths L of the measuring paths) of the measured radiation intensity or preferably of the logarithmic ratio of measured radiation intensity I to the transmitted radiation intensity $I_0$, on the measurable absorption coefficients μ results, which can be calculated or experimentally measured based on the geometry of the measurement chamber. This dependence is determined in a calibration method before start-up and, for example, stored in the form of a characteristic curve in the absorption measurement system. In the following measurement operation, the associated absorption coefficient μ and, in given cases, also other properties of the medium derivable therefrom can now be determined by measuring electronics 7 based on the measured radiation intensities I with reference to the emitted radiation intensity $I_0$ and the characteristic curve.

If all beam paths are selected and utilized as measuring paths, the greatest possible measuring range coverable by the absorption apparatus results due to the different lengths of the measuring paths. This maximum measuring range is clearly greater than measuring ranges, which can be achieved by absorption measurement systems, which have only measuring paths of a single predetermined length.

Since a linearization of the measurement results occurs in any event with the use of this maximal measuring range based on the characteristic curve, a parallel beam guidance of the radiation through measuring chamber 1 can be omitted here.

Alternatively, the selection of the measuring paths M can be predetermined based on the goal of achieving a higher accuracy of measurement in a narrowly limited measuring range within the maximal measuring range. This is always sensible when the range, in which the absorption coefficients μ of the media to be examined lie, is known in advance. The range can, for example, be predetermined based on data on the medium from the user. Alternatively, however, it can preferably be determined fully automatically by the absorption measurement system itself. In this case, the measuring system first performs measurement with the selection of measuring paths, with which the maximum measuring range is achieved as described above. On the basis of these measured absorption coefficients μ, a clearly narrower measuring range surrounding both sides of these absorption coefficients μ can now be fixed. On the basis of this narrower measuring range a renewed selection of measuring paths, with which the highest accuracy of measurement is achievable in a limited measuring range, is now made. Preferably, the subsequently measured absorption coefficients μ are monitored, and the selection of measuring paths is updated as soon as the absorption coefficients μ come to the edge of each previously limited measuring range or leave this measuring range.

In order to achieve a higher accuracy of measurement with the selected measuring paths M in the narrowly limited measuring range, beam paths, which are best suitable due to their length for these limited measuring ranges, are selected from the total beam paths available The selection also preferably occurs here based on the curves of FIG. 5 described above, and the characteristic dependence of the accuracy of measurement of the applied measuring and recording unit 5 on the radiated radiation intensity $I_0$ and the measured radiation intensity relative thereto as well as on their absolute values.

For this, the maximum measuring range can be divided into measuring range portions in advance, and each optimal selection of measuring paths for measurements within the individual measuring range portions as regards the accuracy of measurement are stored in a memory in the absorption measurement system.

Since the selection in this manner of operation no longer comprises all beam paths, the absorption measurement system is embodied in such a manner that transmitting unit 3 transmits radiation through measuring chamber 1 on all measuring paths, and measuring and receiving unit 5 measures the radiation intensities I of the radiation passing through measuring chamber 1 on just the selected measuring paths M.

This can occur, for example, using a system, preferably an electronically controllable aperture 17, inserted in the beam path on the transmission side before measuring chamber 1, as schematically illustrated in FIG. 1. Via a control integrated in measuring electronics 7, for example, the individual apertures 17 of the system can be selected; for example, the measuring paths M1 can be selected for measuring large absorption coefficients μ, the measuring paths M2 can be selected for measuring medium absorption coefficients μ, and the measuring paths M3 can be selected for measuring smaller absorption coefficients μ, or the measuring paths M1, M2 and M3 can be used in parallel for covering the maximal measuring range. In such case, each of those apertures 17, through which each selected measuring paths M extends, are opened by the control.

Alternatively, or supplementally, corresponding apertures can also naturally be applied in the beam path on the receiving side between measuring chamber 1 and measuring and receiving unit 5. This form of embodiment is also especially applicable for frequency dependent intensity measurement in connection with spectrometric measuring and receiving units 5.

Alternatively, the selection of the measuring paths M can also be implemented in a correspondingly embodied measuring and receiving unit 5.

For example, as shown in FIG. 1, the measuring and receiving unit 5 for this can comprise individual detectors 19 arranged in a row or an array; the measurement results of individual detectors 19 are subjected, for example, in the measuring electronics 7 to further processing as a function of their particular separate positions. Diode rows or CCD chips, for example, are suited for this.

The application of individual detectors 19 arranged in a row or an array offers the additional advantage that monitoring of the absorption measurement system is performable with them. For this, a reference intensity profile, which shows a spatial distribution of the intensities measured by individual detectors 19, is registered in advance in a reference measurement with a reference medium in measuring chamber 1. Then, other intensity profiles are registered in the following operation regularly or as needed; the intensity profile then shows each spatial distribution of the intensities present measured by individual detectors 19. Zones, in which an excessively high or low absorption takes place, can be identified by comparing the recorded intensity profiles in measurement operation with the reference profile. In this way, degradations of the measuring system, which affect the absorption behavior within the measuring system locally, can be automatically recognized by the absorption measurement system and displayed. Examples for this are air bubbles in the medium or fouling, such as e.g. deposits, on entrance surface E or exit surface O effecting reinforced or reduced absorption at the site of such occurrence.

Alternatively, the measurement path selection can occur on the receiving side via a point or segment shaped radiation receiver 21, schematically shown in FIG. 2, such as e.g. glass fibers or a glass fiber bundle terminating externally on exit surface O and distributed over exit surface O; the received signals are, for example, subsequently fed to a corresponding number of detectors 23, via which a separated intensity measurement occurs as a function of position. For example, diodes, CCDs, and also spectrometers can be applied as detectors 23 here. In the example of an embodiment illustrated in FIG. 2, four individually selectable regions arise in this way; in these regions, the measuring paths M1, M2, M3, M4 have equal increases in length as one progresses from region to region.

The monitoring method described above is also analogously applicable in this variant.

Another possible implementation of the selection of measuring paths M, likewise shown in FIG. 2, is to provide a plurality of emitters 25, preferably with parallel beam guidance, arranged in a row or an array in transmitting unit 3, for example; emitters 25 can be individually switched on or off.

To the extent that measuring paths M, for example, the measuring paths M1, M2 or M3 shown in FIG. 1, selected for achieving a high accuracy of measurement in a limited measuring range have different lengths due to the measurement chamber geometry, the determination of the absorption coefficients μ preferably occurs likewise according to the above linearizing based on a characteristic curve preferably specially recorded for each selected measuring path.

Additionally, a frequency selective filter F can be provided for individual or all groups of selectable measuring paths M1, M2, M3, M4; the frequency selective filter F is inserted in each case in the associated beam path on the transmission side and/or receiving side. The filter F can be integrated in the associated segments of windows 13 or 15; for example; it can be arranged directly before each of the respective detectors 19, 23; or can be inserted into the corresponding regions of the beam paths between radiation source 9 or radiation sources 25 and entrance surface E in measuring chamber 1 or between exit surface O and measuring and receiving unit 5. Thus filter F for measuring paths M1 illustrated in FIG. 2, can be arranged, for example, as shown here by filter F1, between the associated radiation source 25 and entrance surface E; as shown here by filter F2, directly behind exit surface O, or as shown here by filter F3 directly before the associated detector 23 The application of frequency selective filters F is especially advantageous when properties of media, whose absorption coefficients μ have a clear frequency dependence, should be determined. Preferably, a filter F is provided for each selectable group of measuring paths M1, M2, M3, wherein the filter frequency is matched to the length or to the average length of the measuring paths M of the respective group and preferably to the expected frequency dependence of the absorption coefficient μ to be measured.

The invention claimed is:

1. An absorption measurement system for measuring at least one property of a medium reflected in its absorption behavior, especially a property such as an absorption coefficient of the medium, comprising:

a measuring chamber filled with the medium in measurement operation, in which radiatable beam paths, usable as measuring paths and of different lengths, extend completely through the medium;
a transmitting unit, which transmits radiation along the measuring paths through said measuring chamber in measurement operation;
a measuring and receiving unit, which receives radiation passing through said measuring chamber on the measuring paths and measures its radiation intensities dependent on the property of the medium and the lengths of the measuring paths; and
measuring electronics, which determines the property based on the measured radiation intensities and the lengths of the measuring paths;
wherein said measuring chamber has an entrance surface, through which radiation of said transmission system enters into said measuring chamber, and an exit surface, through which the radiation escapes from said measuring chamber; and
said entrance surface and/or said exit surface is a curved area, especially a convex or concave area.

2. The absorption measurement system as claimed in claim 1, wherein:
said measuring chamber has, in a plane irradiated by said transmitting unit, a wedge shaped cross sectional area, in which the length of the beam paths continuously rises along an axis extending perpendicularly to a main transmission direction of said transmitting unit, in correspondence with an opening angle ($\alpha$) of the wedge shape.

3. The absorption measurement system as claimed in claim 1, wherein:
said measuring chamber has, in a plane irradiated by said transmitting unit, a stepped cross sectional area, in which the length of the beam paths rises stepwise along an axis extending perpendicularly to main transmission direction of said transmitting unit.

4. The absorption measurement system as claimed in claim 1, wherein:
said measuring chamber, especially its entrance or exit surface, has a geometry, which has an optical or mechanical function.

5. The absorption measurement system as claimed in claim 1, wherein:
said measuring paths are a predetermined selection of beam paths, which depends on a measuring range, in which the absorption is to be measured; and
said measuring and receiving unit measures the radiation intensities of the radiation, which passes exclusively through said measuring chamber on the selected measuring paths; and
the radiation intensities are dependent on the absorption in the medium and the lengths of said measuring paths.

6. The absorption measurement system as claimed in claim 1, wherein:
a limited measuring range is predetermined; and
said measuring paths selected from the beam paths are those beam paths, with which a high accuracy of measurement is achieved in this limited measuring range due to their lengths.

7. The absorption measurement system as claimed in claim 1, wherein:
for achieving a maximal measuring range, all beam paths are selected as measuring paths; and
the property is determined based on all radiation intensities from all measuring paths by said measuring and receiving unit.

8. The absorption measurement system as claimed in claim 7, wherein:
there is stored in the absorption measurement system a characteristic curve, which describes a non-linear dependence characteristic for said measuring chamber and predetermined by the lengths of the measuring paths of the radiation intensity impinging on said measuring and receiving unit or the ratio of impinging radiation intensity to the transmitted radiation intensity on the measurable absorption coefficients; and
the absorption coefficient of the medium located in said measuring chamber in measurement operation is determined based on the incoming radiation intensity measured by said measuring and receiving unit and based on the characteristic curve.

9. The absorption measurement system as claimed in claim 1, wherein:
a system of controllable apertures is inserted into the beam paths outside said measuring chamber; and
by controlling said aperture, groups of measuring paths, which extend through said opened aperture or each of said opened apertures, are selectable.

10. The absorption measurement system as claimed in claim 1, wherein:
said measuring and receiving unit comprises individual detectors, especially diodes or CCD's, arranged in a row or an array, and, via these detectors, a separated measurement of the incoming radiation intensities occurs referenced to the positions of said detectors.

11. The absorption measurement system as claimed in claim 1, wherein:
said measuring and receiving unit has point shaped or segment shaped radiation receivers terminating externally on said exit surface and distributed over said exit surface, especially in the form of glass fibers or a glass fiber bundle, each of which receivers is connected to a detector, via which a measurement of the incoming radiation intensities referencing the positions of said associated radiation receiver occurs.

12. A method for monitoring a measuring system as claimed in claim 10, comprising the steps of:
first, a reference intensity profile is recorded in a reference measurement with a reference medium in the measuring chamber; the reference intensity profile reflects a spatial distribution of the radiation intensities measured with the individual detectors;
other intensity profiles are recorded in following measurement operation, the intensity profiles reflect each spatial distribution of the radiation intensities then currently present as measured by the individual detectors; and
a comparison of the recorded intensity profiles in measurement operation with the reference profile is made to monitor whether zones with an excessively high or low absorption occur in the recorded intensity profiles.

13. The absorption measurement system as claimed in claim 1, wherein:
said transmitting unit comprises a plurality of emitters, especially emitters with parallel beam guidance, arranged in a row or an array, said emitters can be individually switched on or off as a function of the selection of measuring paths.

14. The absorption measurement system as claimed in claim 1, wherein:
individual predetermined groups of measuring paths are selectable; and
a frequency selective filter, which is applied in the beam path outside said measuring chamber, is provided for at least one of the groups.

15. The method for the operation of an absorption measurement system as claimed in claim 5, comprising the steps:
- a first measurement is executed with a selection of measuring paths, in the case of which the measuring system has the maximal measuring range;
- based on this measurement, a narrower measuring range, in which the measurement result of the first measuring lies, is established;
- based on this narrower measuring range, a renewed selection of measuring paths, with which the highest accuracy of measurement in this limited measuring range is achievable, is made; and
- following measurements are executed based on this selection of measuring paths made for the limited measuring range.

16. The method as claimed in claim 15, wherein:
the measurement results of the following measurements are monitored, and the selection of measuring paths is updated as soon as the measurement results come to the edge of each limited measuring range last applied or leave this limited measuring range.

17. An absorption measurement system for measuring at least one property of a medium reflected in its absorption behavior, especially a property such as an absorption coefficient of the medium, comprising:
- a measuring chamber filled with the medium in measurement operation, in which radiatable beam paths, usable as measuring paths and of different lengths, extend completely through the medium;
- a transmitting unit, which transmits radiation along the measuring paths through said measuring chamber in measurement operation;
- a measuring and receiving unit, which receives radiation passing through said measuring chamber on the measuring paths and measures its radiation intensities dependent on the property of the medium and the lengths of the measuring paths; and
- measuring electronics, which determines the property based on the measured radiation intensities and the lengths of the measuring paths;
- wherein said transmitting unit comprises a plurality of emitters, especially emitters with parallel beam guidance, arranged in a row or an array, said emitters can be individually switched on or off as a function of the selection of measuring paths.

18. An absorption measurement system for measuring at least one property of a medium reflected in its absorption behavior, especially a property such as an absorption coefficient of the medium, comprising:
- a measuring chamber filled with the medium in measurement operation, in which radiatable beam paths, usable as measuring paths and of different lengths, extend completely through the medium;
- a transmitting unit, which transmits radiation along the measuring paths through said measuring chamber in measurement operation;
- a measuring and receiving unit, which receives radiation passing through said measuring chamber on the measuring paths and measures its radiation intensities dependent on the property of the medium and the lengths of the measuring paths; and
- measuring electronics, which determines the property based on the measured radiation intensities and the lengths of the measuring paths;
- wherein individual predetermined groups of measuring paths are selectable; and
- a frequency selective filter, which is applied in the beam path outside said measuring chamber, is provided for at least one of the groups.

* * * * *